(12) United States Patent
Tisdall et al.

(10) Patent No.: US 10,045,741 B2
(45) Date of Patent: Aug. 14, 2018

(54) SYSTEM AND METHOD FOR REAL-TIME FREQUENCY CORRECTION FOR MAGNETIC RESONANCE IMAGING

(71) Applicants: Matthew Tisdall, Somerville, MA (US); Andre van der Kouwe, Woburn, MA (US)

(72) Inventors: Matthew Tisdall, Somerville, MA (US); Andre van der Kouwe, Woburn, MA (US)

(73) Assignee: The General Hospital Corporation, Boston, MA (US)

( * ) Notice: Subject to any disclaimer, the term of this patent is extended or adjusted under 35 U.S.C. 154(b) by 859 days.

(21) Appl. No.: 14/449,297

(22) Filed: Aug. 1, 2014

(65) Prior Publication Data

US 2015/0035530 A1    Feb. 5, 2015

Related U.S. Application Data

(60) Provisional application No. 61/861,672, filed on Aug. 2, 2013.

(51) Int. Cl.
| | |
|---|---|
| *G01R 33/565* | (2006.01) |
| *A61B 5/00* | (2006.01) |
| *A61B 5/055* | (2006.01) |
| *G01R 33/561* | (2006.01) |
| *A61B 5/08* | (2006.01) |

(52) U.S. Cl.
CPC ............ *A61B 5/7285* (2013.01); *A61B 5/055* (2013.01); *A61B 5/7203* (2013.01); *G01R 33/565* (2013.01); *A61B 5/0816* (2013.01); *G01R 33/5616* (2013.01); *G01R 33/56509* (2013.01); *G01R 33/56518* (2013.01); *G01R 33/56563* (2013.01)

(58) Field of Classification Search
CPC .............. G01R 33/5616; G01R 33/565; G01R 33/56509; G01R 33/56518; G01R 33/56563; A61B 5/7285; A61B 5/0816; A61B 5/7203; A61B 5/055
See application file for complete search history.

(56) References Cited

U.S. PATENT DOCUMENTS

| | | | |
|---|---|---|---|
| 6,064,206 A | 5/2000 | Van Vaals et al. | |
| 2008/0154119 A1 | 6/2008 | Lewin et al. | |
| 2011/0268332 A1 | 11/2011 | Hofstetter et al. | |
| 2013/0187649 A1 | 7/2013 | Bhat et al. | |
| 2015/0035530 A1* | 2/2015 | Tisdall ................. | A61B 5/7285 324/307 |
| 2017/0059682 A1* | 3/2017 | Dagher ................ | G01R 33/243 |

OTHER PUBLICATIONS

International Search Report and Written Opinion for international application No. PCT/US2014/049378; dated Oct. 16, 2014; 6 pages.

* cited by examiner

*Primary Examiner* — Dixomara Vargas
(74) *Attorney, Agent, or Firm* — Quarles & Brady LLP

(57) ABSTRACT

Systems and methods for estimating frequency drifts in magnetic resonance signals acquired with a magnetic resonance imaging ("MRI") system are provided. In one example, the frequency drifts are estimated from phase-correction data that are obtained during an echo-planar imaging ("EPI"), or other multiecho imaging, scan. The systems and methods of the present invention provide for efficiently and accurately computing frequency drift values that can be used for real-time, prospective frequency drift correction.

13 Claims, 2 Drawing Sheets

SYSTEM AND METHOD FOR REAL-TIME FREQUENCY CORRECTION FOR MAGNETIC RESONANCE IMAGING

CROSS-REFERENCE TO RELATED APPLICATIONS

This application claims the benefit of U.S. Provisional Patent Application Ser. No. 61/861,672, filed on Aug. 2, 2013, and entitled "SYSTEM AND METHOD FOR REAL-TIME FREQUENCY CORRECTION FOR MAGNETIC RESONANCE IMAGING."

STATEMENT REGARDING FEDERALLY SPONSORED RESEARCH

This invention was made with government support under HD071664 awarded by National Institutes of Health. The government has certain rights in the invention.

BACKGROUND OF THE INVENTION

The field of the invention is systems and methods for magnetic resonance imaging ("MRI"). More particularly, the invention relates to systems and methods for correcting frequency drifts and associated errors in real-time during an MRI scan.

Pulse sequences with high gradient duty cycles can produce heating that, in turn, leads to a gradual drift in the resonance frequency. Frequency fluctuations can also be caused by subject respiration and motion. Volumetric navigators ("vNavs") based on 3D-encoded EPI for tracking subject motion can be used when embedded in 3D-encoded morphometry scans. Paired vNavs with shifted echo times can be used for frequency and shim correction. These sequences, however, require additional scan time.

It would therefore be desirable to provide a system and method that allows the shift in resonance frequency, or frequency drift, to be measured reliably from a single vNav without expending any additional scan time.

SUMMARY OF THE INVENTION

The present invention overcomes the aforementioned drawbacks by providing a method for estimating frequency-drift errors in a magnetic resonance signal acquired with a magnetic resonance imaging ("MRI") system. Data is acquired by directing the MRI system to perform a pulse sequence that samples multiple echo signals in each repetition time ("TR") period, such as an echo-planar imaging ("EPI") pulse sequence or an EPI pulse sequence that also includes acquiring volumetric navigator signals. Reference data is selected from the acquired data. For instance, the reference data may be selected as the data acquired in the first TR. From the acquired data, a phase offset value is computed. This phase offset value is related to a frequency drift in data acquired during a given TR period relative to the selected reference data. A frequency drift value is then estimated from the computed phase offset values.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Systems and methods for estimating frequency drifts in magnetic resonance signals acquired with a magnetic resonance imaging ("MRI") system are provided. In one example, the frequency drifts are estimated from phase-correction data that are obtained during an echo-planar imaging ("EPI"), or other multiecho imaging, scan. The systems and methods of the present invention provide for efficiently and accurately computing frequency drift values that can be used for real-time, prospective frequency drift correction.

In some embodiments, the system and method of the present invention can implement volumetric navigators ("vNavs") when estimating the frequency drift values. These EPI-based navigators are embedded in a longer parent scan and have previously been used for motion correction. Here, however, the vNavs can be used for frequency drift correction.

Advantageously, the frequency drift correction technique described here can be embedded in a system as part of a motion-correction sequence without changing the navigators. This, in turn, improves the quality of motion correction.

Figure 1:
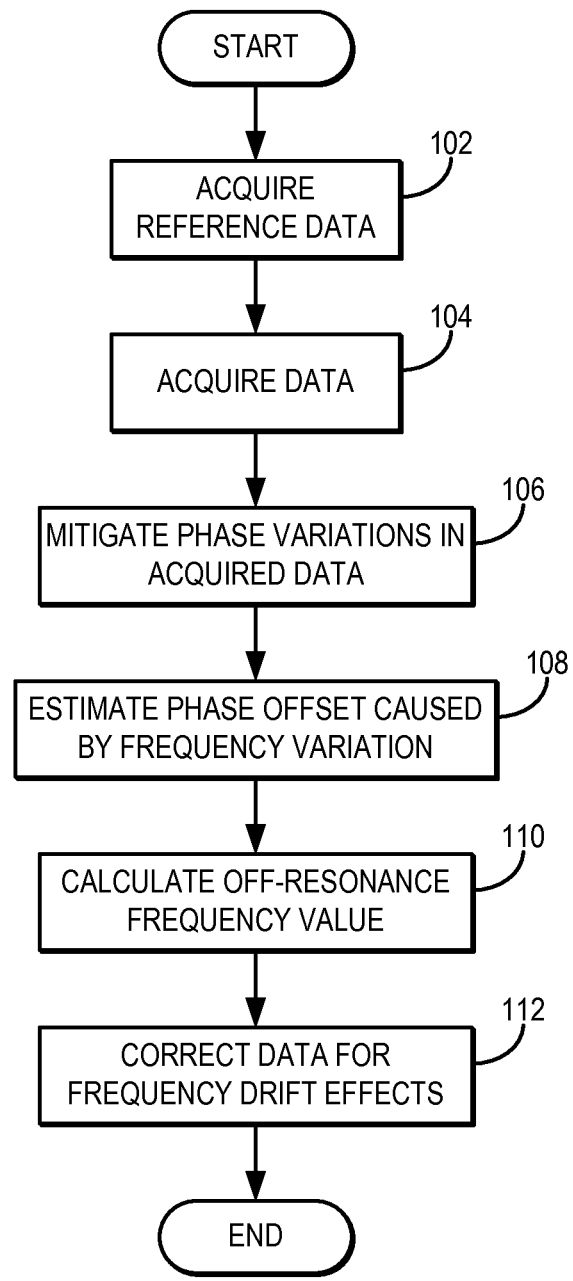
FIG. 1 is a flowchart setting forth the steps of an example of a method for estimating frequency drifts in magnetic resonance signals.

Referring now to FIG. 1, a flowchart setting forth the steps of an example of a method for estimating frequency drifts in magnetic resonance signals is illustrated. The method begins with the acquisition of reference data, as illustrated at step 102. In general, the reference data is simply the data acquire in the first repetition time ("TR") period of the pulse sequence utilized to acquire data. Examples of pulse sequences that can be utilized when implementing the present invention include echo-planar imaging ("EPI") pulse sequences and other multiecho pulse sequences, such as multiecho-MPRAGE ("MEMPRAGE"). Next, additional data is acquired with the MRI system, as illustrated at step 104. Generally speaking, the additional data is acquired with the same pulse sequence as the reference data. For instance, if an EPI pulse sequence that acquires phase-correction lines is utilized in step 102, a similar pulse sequence will be used in step 104.

By way of example, the EPI sequence used to acquire data may be a vNav EPI sequence. To enable accurate frequency estimation, the vNav sequence can include an increased number of alternating, blip-less readouts after the first excitation pulse. This fills the previous dead time after the first pulse without modifying any of the other timing parameters of the vNav acquisition, without adding extra excitation pulses, and without adding any time to the vNav. An example of the pulse sequence may include a 3D-encoded acquisition using three-quarter partial Fourier encoding in the partition direction and twenty-five excitation pulses. Data is acquired after the first excitation pulse as noted above and, after each of the last twenty-four pulses, EPI readout lines for a single partition that cover almost all the available time between excitation pulses are acquired.

Phase variations, such as those from eddy currents and similar sources, are mitigated in the acquired data using the reference data, as indicated at step 106. By way of example, these phase variations can be mitigated by pointwise multiplying the acquired data by the conjugate of the reference data, $$\tilde{s}_k[i] = s_k[i] \cdot s_{ref}^*[i] \text{ for } i=1,\ldots,N \quad (1);$$

where $\tilde{s}_k[i]$ is the phase-variation mitigated data for the $i^{th}$ k-space line in the $k^{th}$ TR period, $s_k[i]$ is the data acquired for the $i^{th}$ k-space line in the $k^{th}$ TR period, and $s_{ref}^*[i]$ is the conjugate of the reference data for the $i^{th}$ k-space line. The acquired data, $s_k$, is composed of N total lines of k-space data.

The phase offset resulting from the frequency drift is estimated from the phase-variation mitigated data next, as indicated at step 108. By way of example, this step includes computing phase offset data as, $$\hat{s}_k[i] = \tilde{s}_k[i] \tilde{s}_k^*[i+1] \text{ for } i=1,\ldots,N-1 \quad (2);$$

where $\hat{s}_k[i]$ is phase offset data whose phase value is equivalent to the phase difference between the $i^{th}$ and $(i+1)^{th}$ k-space line in the data acquired in the $k^{th}$ TR period. It is noted that the phase offset data will include one less line of data than the originally acquired data. The phase value of the phase offset data, $\hat{s}_k$, can thus be computed as an estimate of the phase offset resulting from the frequency drift.

The frequency drift, or off-resonance frequency value, is then estimated from the calculated phase offset data, as indicated at step 110. By way of example, the off-resonance frequency value can be calculated by dividing the phase value of the complex average of the phase offset data by the echo spacing of the pulse sequence used to acquire the data. This complex average can be computed across all lines of k-space in the phase offset data, the central readout points of k-space, and across all channels if a multichannel receiver coil array is implemented. This complex average performs a weighted average where the signal amplitudes have been squared in steps 106 and 108 so that the most reliable signals have more impact on the complex average.

The originally acquired data, or the phase-variation mitigated data, can then be corrected for the effects of frequency drift using the estimated frequency shift value, as indicated at step 112. For instance, the original data can be corrected as, $$s_{k,corr}(t) = s_k(t) \cdot e^{-i\Delta f_k t} \quad (3);$$

and the phase-variation mitigated data can be corrected as, $$\tilde{s}_{k,corr}(t) = \tilde{s}_k(t) e^{-i\Delta f_k t} \quad (4);$$

where $\Delta f_k$ is the estimated frequency drift value for the data acquired in the $k^{th}$ TR period.

Figure 2:
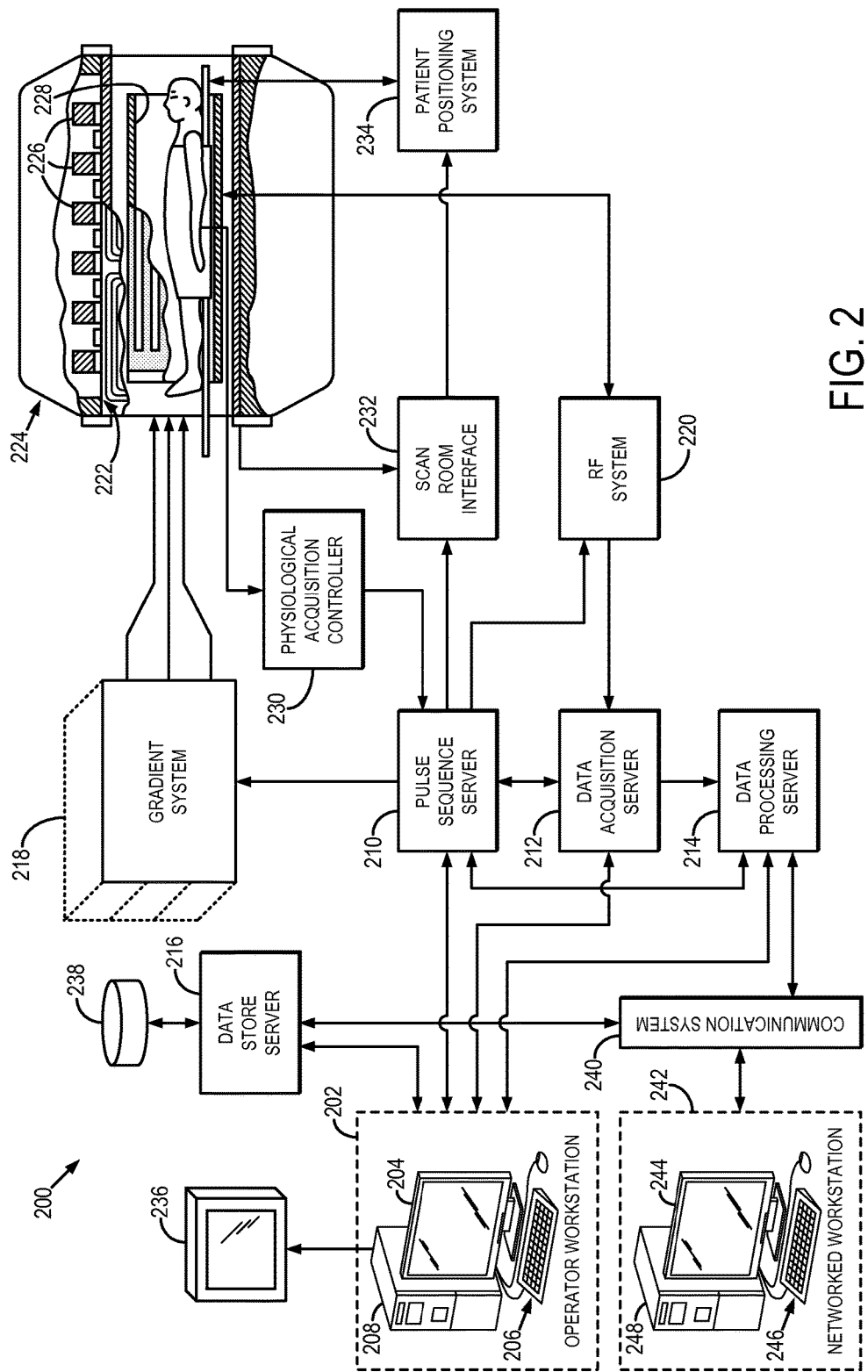
FIG. 2 is a block diagram of an example of a magnetic resonance imaging ("MRI") system.

Referring particularly now to FIG. 2, an example of a magnetic resonance imaging ("MRI") system 200 is illustrated. The MRI system 200 includes a workstation 202 having a display 204 and a keyboard 206. The workstation 202 includes a processor 208, such as a commercially available programmable machine running a commercially available operating system. The workstation 202 provides the operator interface that enables scan prescriptions to be entered into the MRI system 200. The workstation 202 is coupled to four servers: a pulse sequence server 210; a data acquisition server 212; a data processing server 214; and a data store server 216. The workstation 202 and each server 210, 212, 214, and 216 are connected to communicate with each other.

The pulse sequence server 210 functions in response to instructions downloaded from the workstation 202 to operate a gradient system 218 and a radiofrequency ("RF") system 220. Gradient waveforms necessary to perform the prescribed scan are produced and applied to the gradient system 218, which excites gradient coils in an assembly 222 to produce the magnetic field gradients $G_x$, $G_y$, and $G_z$ used for position encoding MR signals. The gradient coil assembly 222 forms part of a magnet assembly 224 that includes a polarizing magnet 226 and a whole-body RF coil 228.

RF excitation waveforms are applied to the RF coil 228, or a separate local coil (not shown in FIG. 2), by the RF system 220 to perform the prescribed magnetic resonance pulse sequence. Responsive MR signals detected by the RF coil 228, or a separate local coil (not shown in FIG. 2), are received by the RF system 220, amplified, demodulated, filtered, and digitized under direction of commands produced by the pulse sequence server 210. The RF system 220 includes an RF transmitter for producing a wide variety of RF pulses used in MR pulse sequences. The RF transmitter is responsive to the scan prescription and direction from the pulse sequence server 210 to produce RF pulses of the desired frequency, phase, and pulse amplitude waveform. The generated RF pulses may be applied to the whole body RF coil 228 or to one or more local coils or coil arrays (not shown in FIG. 2).

The RF system 220 also includes one or more RF receiver channels. Each RF receiver channel includes an RF preamplifier that amplifies the MR signal received by the coil 228 to which it is connected, and a detector that detects and digitizes the and Q quadrature components of the received MR signal. The magnitude of the received MR signal may thus be determined at any sampled point by the square root of the sum of the squares of the I and Q components:

$$M = \sqrt{I^2 + Q^2} \quad (5);$$

and the phase of the received MR signal may also be determined:

$$\varphi = \tan^{-1}\left(\frac{Q}{I}\right). \quad (6)$$

The pulse sequence server 210 also optionally receives patient data from a physiological acquisition controller 230. The controller 230 receives signals from a number of different sensors connected to the patient, such as electrocardiograph ("ECG") signals from electrodes, or respiratory signals from a bellows or other respiratory monitoring device. Such signals are typically used by the pulse sequence server 210 to synchronize, or "gate," the performance of the scan with the subject's heart beat or respiration.

The pulse sequence server 210 also connects to a scan room interface circuit 232 that receives signals from various sensors associated with the condition of the patient and the magnet system. It is also through the scan room interface circuit 232 that a patient positioning system 234 receives commands to move the patient to desired positions during the scan.

The digitized MR signal samples produced by the RF system 220 are received by the data acquisition server 212. The data acquisition server 212 operates in response to instructions downloaded from the workstation 202 to receive the real-time MR data and provide buffer storage, such that no data is lost by data overrun. In some scans, the data acquisition server 212 does little more than pass the acquired MR data to the data processor server 214. However, in scans that require information derived from acquired MR data to control the further performance of the scan, the data acquisition server 212 is programmed to produce such information and convey it to the pulse sequence server 210. For example, during prescans, MR data is acquired and used to calibrate the pulse sequence performed by the pulse sequence server 210. Also, navigator signals may be acquired during a scan and used to adjust the operating parameters of the RF system 220 or the gradient system 218, or to control the view order in which k-space is sampled. In all these examples, the data acquisition server 212 acquires MR data and processes it in real-time to produce information that is used to control the scan.

The data processing server 214 receives MR data from the data acquisition server 212 and processes it in accordance with instructions downloaded from the workstation 202. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 214 are conveyed back to the workstation 202 where they are stored. Real-time images are stored in a data base memory cache (not shown in FIG. 2), from which they may be output to operator display 212 or a display 236 that is located near the magnet assembly 224 for use by attending physicians. Batch mode images or selected real time images are stored in a host database on disc storage 238. When such images have been reconstructed and transferred to storage, the data processing server 214 notifies the data store server 216 on the workstation 202. The workstation 202 may be used by an operator to archive the images, produce films, or send the images via a network to other facilities.

Thus, systems and methods for high-quality, real-time resonance frequency estimates in addition to real-time motion estimates have been provided. A gradually shifting resonance frequency can induce an artificial motion in the phase-encode direction, confounding motion estimates. By updating the reference frequency, the accuracy of motion estimates over long scans is improved.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for estimating frequency-drift errors in a magnetic resonance signal acquired with a magnetic resonance imaging (MRI) system, the steps of the method comprising:
    a) acquiring data with the MRI system by directing the MRI system to perform a pulse sequence that samples multiple echo signals in each repetition time (TR) period;
    b) selecting reference data from the acquired data using a computer system;
    c) computing with the computer system, phase offset values based on the acquired data and the selected reference data, wherein the phase offset values are related to a frequency drift in data acquired during a given TR period relative to the selected reference data; and
    d) estimating with the computer system, a frequency drift value from the computed phase offset values.

2. The method as recited in claim 1 further comprising correcting with the computer system, the acquired data for errors associated with the frequency drift using the estimated frequency drift value.

3. The method as recited in claim 1 wherein the reference data is selected using the computer system as data acquired in a first TR period.

4. The method as recited in claim 1 wherein step c) includes mitigating phase variations in the acquired data using the computer system before computing the phase offset value.

5. The method as recited in claim 4 in which the phase variations are mitigated by pointwise multiplying the acquired data for a given TR period by a conjugate of the reference data using the computer system.

6. The method as recited in claim 1 wherein step c) includes computing phase offset data with the computer system by pointwise multiplying each line of data by a conjugate of that line of data shifted by one line in a direction corresponding to gradient blips applied during data acquisition in step a).

7. The method as recited in claim 6 wherein step c) includes mitigating phase variations in the acquired data using the computer system before computing the phase offset data using the computer system.

8. The method as recited in claim 7 wherein the phase variations are mitigated using the computer system by pointwise multiplying the acquired data for a given TR period by a conjugate of the reference data.

9. The method as recited in claim 6 wherein the phase offset value is computed using the computer system by calculating a complex average of the phase offset data and computing a phase value of the complex averaged phase offset data.

10. The method as recited in claim 1 wherein step d) includes dividing the phase offset value by an echo spacing time implemented during data acquisition in step a) using the computer system.

11. The method as recited in claim 1 wherein data is acquired with the MRI system in step a) using an echo-planar imaging pulse sequence.

12. The method as recited in claim 1 wherein data is acquired with the MRI system in step a) using a pulse sequence that includes acquiring volumetric navigator data.

13. The method as recited in claim 2, further comprising reconstructing with the computer system, an image from the acquired data that has been corrected for errors associated with the frequency drift using the estimated frequency drift value, wherein the image has reduced errors associated with the frequency drift as compared to an image reconstructed from the acquired data without correcting for errors associated with the frequency drift.

* * * * *